(12) United States Patent
McNamara et al.

(10) Patent No.: US 11,109,994 B2
(45) Date of Patent: Sep. 7, 2021

(54) DEVICE FOR THE TREATMENT OF MEDIAL TIBIAL STRESS SYNDROME AND OTHER CONDITIONS OF THE LOWER LEG

(71) Applicant: Ossyx Pty Ltd, Epping (AU)

(72) Inventors: William John McNamara, Daleys Point (AU); Rosa Marguerite Miller, Daleys Point (AU); Benjamin James Richard Lindsay, Daleys Point (AU)

(*) Notice: Subject to any disclaimer, the term of this patent is extended or adjusted under 35 U.S.C. 154(b) by 650 days.

(21) Appl. No.: 15/766,378

(22) PCT Filed: Oct. 6, 2016

(86) PCT No.: PCT/AU2016/000342
§ 371 (c)(1),
(2) Date: Apr. 6, 2018

(87) PCT Pub. No.: WO2017/059478
PCT Pub. Date: Apr. 13, 2017

(65) Prior Publication Data
US 2018/0289526 A1 Oct. 11, 2018

(30) Foreign Application Priority Data
Oct. 6, 2015 (AU) ................................ 2015904068

(51) Int. Cl.
*A61F 5/00* (2006.01)
*A61F 5/058* (2006.01)
(Continued)

(52) U.S. Cl.
CPC ........ *A61F 5/0585* (2013.01); *A41D 13/0543* (2013.01); *A61F 5/32* (2013.01);
(Continued)

(58) Field of Classification Search
CPC .. A61F 5/0585; A61F 5/32; A61F 5/34; A61F 13/08; A61F 13/085; A61F 13/061;
(Continued)

(56) References Cited

U.S. PATENT DOCUMENTS 3,934,583 A 1/1976 Hollingshead
8,109,964 B2 2/2012 Korrol
(Continued)

FOREIGN PATENT DOCUMENTS

WO 2012/131298 10/2012

*Primary Examiner* — Kim M Lewis
(74) *Attorney, Agent, or Firm* — Darren Gardner (57) ABSTRACT

A calf brace for the treatment of MTSS (shin splints) and other conditions of the lower leg, including the foot, includes a strap arrangement that is used to locate pressure nodes that target specific areas of a wearer's calf muscle to facilitate release of the calf muscle. In one embodiment, the straps are anchored to a sleeve that can be pulled onto the wearer's calf muscle over the foot. Targeted zones may include the point on the calf where the soleus muscle attaches to the posterior head of the fibula, the point where the soleus muscle attaches to the middle third of the tibia; and the back of the calf at approximately the junction of the Achilles tendon and the triceps surae muscle. A compressive rod may also be aligned with approximately the distal one third of the medial border of the tibia where periosteal elevation and inflammation is thought to occur.

20 Claims, 9 Drawing Sheets

(51) Int. Cl.
  *A61F 5/32*  (2006.01)
  *A41D 13/05*  (2006.01)
  *A61F 13/08*  (2006.01)
(52) U.S. Cl.
  CPC .......... *A41D 2400/32* (2013.01); *A61F 13/08* (2013.01); *A61H 2201/164* (2013.01)
(58) Field of Classification Search
  CPC .............. A61F 13/062; A41D 13/0543; A41D 2400/32; A41D 2400/322; A41D 2400/324; A63B 2225/50; A63B 2220/12; A63B 2220/803; A63B 2220/20; A63B 2220/51; A63B 2220/807; A63B 2230/60; A63B 2220/40; A63B 2220/836; A63B 2220/30; A63B 2220/74; A63B 2220/833; A63B 2225/74; A63B 24/0062; A63B 69/0028; A63B 2220/13; A63B 2220/24; A63B 2220/72; A63B 2225/54; A63B 2230/06; A63B 2071/1233; A63B 2071/125; A63B 2071/1283; A63B 21/072; A63B 21/0724; A63B 21/0726; A63B 2220/16; A63B 2220/53; A63B 2220/56; A63B 2220/75; A63B 2220/76; A63B 2220/806; A63B 2225/30; A63B 2230/70; A63B 2243/0025; A63B 2243/0037; A63B 2243/0054; A63B 2243/0066; A63B 2243/007; A63B 2243/0095; A63B 2244/102; A63B 2244/18; A63B 2244/19; A63B 2244/20; A63B 2244/203; A63B 69/0002; A63B 69/0026; A63B 69/0048; A63B 69/0071; A63B 69/02; A63B 69/06; A63B 69/16; A63B 69/36; A63B 69/3632; A63B 71/085; A63B 71/10; A63B 71/1216; A63B 71/1291; A63B 71/141; A63B 71/145; A63B 2230/04; A63B 43/004; A63B 60/46; A63B 69/38; A63B 24/0006; A63B 24/0075; A63B 71/06; A63B 2208/0204; A63B 2230/50; A63B 24/0021; A63B 2209/10; A63B 2220/17; A63B 2024/0071; A63B 21/4039; A63B 21/4043; A63B 2230/75; A63B 2024/0096; A63B 2071/0625; A63B 21/0557; A63B 2209/00; A63B 2220/54; A63B 2225/20; A63B 2024/0009; A63B 2024/0065; A63B 2024/0068; A63B 2024/0081; A63B 2071/063; A63B 2071/0675; A63B 21/00178; A63B 21/00181; A63B 21/0058; A63B 21/068; A63B 21/4007; A63B 21/4015; A63B 21/4025; A63B 21/4027; A63B 21/4035; A63B 21/4047; A63B 2220/62; A63B 2220/80; A63B 2220/808; A63B 2230/00; A63B 23/0405; A63B 24/0087; A63B 71/0054; A63B 71/0622; A63B 1/00; A63B 2023/006; A63B 2023/0411; A63B 2024/0012; A63B 2024/0015; A63B 2071/0647; A63B 2071/0655; A63B 2071/0694; A63B 2102/32; A63B 21/0004; A63B 21/0005; A63B 21/00054; A63B 21/00061; A63B 21/0023; A63B 21/02; A63B 21/022; A63B 21/0428; A63B 21/0435; A63B 21/0552; A63B 21/0555; A63B 21/06; A63B 21/0622; A63B 21/0628; A63B 21/065; A63B 21/078; A63B 21/152; A63B 21/156; A63B 21/4009; A63B 21/4011; A63B 21/4013; A63B 21/4029; A63B 21/4031; A63B 21/4034; A63B 2208/02; A63B 2208/0223; A63B 2208/0228; A63B 2208/0271; A63B 2208/0285; A63B 2208/05; A63B 2209/02; A63B 2210/50; A63B 2213/00; A63B 2220/10; A63B 2220/50; A63B 2220/801; A63B 2220/805; A63B 2225/09; A63B 2225/093; A63B 2225/096; A63B 2225/102; A63B 2225/66; A63B 2230/01; A63B 2230/10; A63B 2230/105; A63B 2230/30; A63B 2230/605; A63B 22/02; A61B 5/0022; A61B 2562/0219; A61B 5/6804; A61B 2503/10; A61B 5/11; A61B 5/024; A61B 5/0402; A61B 5/6895; A61B 5/01; A61B 5/0205; A61B 5/053; A61B 5/0533; A61B 5/055; A61B 5/4872; A61B 5/6806; A61B 5/1118; A61B 5/112; A61B 5/6812; A61B 5/6828; A61B 5/002; A61B 5/0024; A61B 5/021; A61B 5/1123; A61B 2505/09; A61B 5/02141; A61B 5/1114; A61B 5/1116; A61B 5/1121; A61B 5/4836; A61B 5/4842; A61B 5/4848; A61B 5/681; A61B 5/6824; A61B 5/7267; A61B 5/7275; A61B 2503/20; A61B 5/02007; A61B 5/02042; A61B 5/022; A61B 5/0295; A61B 5/0488; A61B 5/418; A61B 5/4238; A61B 5/4255; A61B 5/6803; A61B 5/6811; A61B 5/6829; A61B 5/7455; A61B 2505/07; A61B 2562/04; A61B 5/02416; A61B 5/0476; A61B 5/1112; A61B 5/1126; A61B 5/486; A61B 5/6805; A61B 5/6831; A61B 5/7282; A61B 5/743; A61B 6/037; A61B 6/4258; A61B 6/4266; A61B 6/4275; A61B 6/4405; A61B 6/4429; A61B 6/501; A61B 6/506; A61B 2017/00022; A61B 2017/00411; A61B 2090/064; A61B 2560/0242; A61B 2562/0247; A61B 2562/222; A61B 5/0077; A61B 5/02055; A61B 5/02438; A61B 5/0245; A61B 5/0255; A61B 5/0275; A61B 5/04004; A61B 5/0428; A61B 5/224; A61B 5/6807; A61B 5/6843; A61B 5/7214; A61B 5/7225; A61B 5/725; A61B 5/7271; A61B 5/7405; A61B 5/7465; A61B 6/04; A61B 6/481; A61B 17/00491; A61B 17/0057; A61B 17/12118; A61B 17/12181; A61B 17/1322; A61B 17/1703; A61B 17/3468; A61B 18/18; A61B 2017/00084; A61B 2017/00207; A61B 2017/0023; A61B 2017/00402; A61B 2017/00526; A61B 2017/0065; A61B 2017/00862; A61B 2017/00871; A61B 2017/00876; A61B 2017/1205; A61B 2034/102; A61B 2034/105; A61B 2034/107; A61B 2034/108; A61B 2034/2065; A61B 2090/365; A61B 2090/372; A61B 2090/3983; A61B 2503/12; A61B 2503/40; A61B 2505/01; A61B 2505/03; A61B 2560/0219; A61B 2560/045; A61B 2562/0271; A61B 2562/043; A61B 2562/12; A61B 2562/225; A61B 34/10;
A61B 5/00; A61B 5/0004; A61B 5/0053;
A61B 5/0225; A61B 5/02405; A61B
5/0261; A61B 5/02755; A61B 5/0404;
A61B 5/046; A61B 5/0464; A61B
5/0482; A61B 5/05; A61B 5/0537; A61B
5/073; A61B 5/1036; A61B 5/1038; A61B
5/1071; A61B 5/1073; A61B 5/1115;
A61B 5/1124; A61B 5/1127; A61B
5/1128; A61B 5/14535; A61B 5/14551;
A61B 5/14552; A61B 5/163; A61B
5/165; A61B 5/18; A61B 5/4064; A61B
5/442; A61B 5/443; A61B 5/445; A61B
5/447; A61B 5/4504; A61B 5/4514; A61B
5/4519; A61B 5/4523; A61B 5/4528;
A61B 5/4533; A61B 5/4561; A61B
5/4585; A61B 5/4878; A61B 5/6802;
A61B 5/6813; A61B 5/6826
USPC .............................................. 602/23; 601/33
See application file for complete search history.

(56) References Cited

U.S. PATENT DOCUMENTS

| | | | |
|---|---|---|---|
| 9,795,499 B2* | 10/2017 | Ponce | A61H 1/0237 |
| 2004/0015117 A1* | 1/2004 | Gauthier | A41D 17/00 |
| | | | 602/62 |
| 2013/0085426 A1 | 4/2013 | Brodsky | |
| 2013/0281903 A1 | 10/2013 | Kozasa | |
| 2013/0282046 A1* | 10/2013 | Ravikumar | A61F 13/085 |
| | | | 606/201 |
| 2014/0276259 A1 | 9/2014 | Smart | |
| 2015/0073317 A1* | 3/2015 | Cox | A61F 5/30 |
| | | | 601/84 |
| 2015/0119781 A1 | 4/2015 | Corpus Sanus | |
| 2015/0165339 A1 | 6/2015 | Luebke et al. | |
| 2016/0000612 A1* | 1/2016 | Cox | A61H 1/008 |
| | | | 602/62 |

* cited by examiner

DEVICE FOR THE TREATMENT OF MEDIAL TIBIAL STRESS SYNDROME AND OTHER CONDITIONS OF THE LOWER LEG

CROSS REFERENCE TO RELATED APPLICATIONS

This application is related to and claims the priority benefit of Australian Provisional Application No. 2015904068 filed 6 Oct. 2015, the entire contents of which are herein incorporated by reference.

FIELD OF THE INVENTION

This invention relates to a device and method for the treatment of medial tibial stress syndrome (MTSS), commonly referred to as "shin splints". The invention may also have application for treatment of other lower leg conditions, including conditions of the foot, that benefit from release of the calf muscle.

BACKGROUND TO THE INVENTION

Shin splints or MTSS, is an overuse injury or repetitive-stress injury of the shin area. A range of stress reactions of the tibia and surrounding musculature occur when the body is unable to heal properly in response to repetitive muscle contractions and tibial strain.

MTSS occurs in approximately 4-20% of the general population and has significantly increased prevalence in athletes, particularly runners.

The most common complaint is vague, diffuse pain of the lower extremity along the middle to distal tibia and is associated with exertion. Clinical examination of the distal one-third of the medial border of the tibia often reveals tenderness to light palpation with the anterior tibia often being non-tender. Patients with early phase MTSS experience the worst pain at the beginning of exercise and this gradually subsides during training or within minutes of cessation of exercise. As the disease progresses the pain presents with less activity and may occur at rest.

The pathophysiology is not well understood, however, it is believed to be a combination of tendinopathy, periostitis, periosteal remodelling, and stress reaction of the tibia.

There are multiple risk factors for developing MTSS, however, muscle imbalance and inflexibility, especially tightness of the triceps surae (gastrocnemius, soleus, and plantaris muscles) has been documented heavily in the literature as being commonly associated with MTSS.

Treatment to date has been predominantly conservative (rest, ice, analgesia, stretching, massage), however, few advances have been made in the treatment of MTSS over the last few decades. Rest has been shown to be the single most important treatment in acute MTSS. For many athletes, however, prolonged rest is not ideal.

Other treatments include use of NSAIDs and ice for analgesia. Physiotherapy has been shown to be helpful, however, many athletes require more regular treatment suggesting an athlete self-directed method of treatment is perhaps needed. As agreed upon by a large body of evidence, the key to treatment of MTSS is prevention.

SUMMARY OF THE INVENTION

In essence the invention provides a calf brace that will encircle the wearer's calf and apply, at selected positions on the calf, elevated pressure points. Optionally, the calf brace may also be used to provide a torsional force to the wearer's calf muscle to further aid in the release of the calf muscle.

In one aspect, there is provided a calf brace for treating a condition of a lower leg of a subject, the calf brace including:
 (A) a plurality of straps configured to extend around at least a portion of a calf muscle of the subject;
 (B) a plurality of pressure nodes that in use, are located between the plurality of straps and the calf muscle, the plurality of pressure nodes configured to apply elevated pressure inward to a plurality of targeted zones of the calf muscle when one or more of the plurality of straps are tightened around the calf muscle;
 (C) wherein the plurality of targeted zones includes at least two of:
  (a) the approximate point on the calf where the soleus muscle attaches to the posterior head of the fibula;
  (b) the approximate point where the soleus muscle attaches to the middle third of the tibia; and
  (c) the back of the calf at approximately the junction of the Achilles tendon and the triceps surae muscle.

In one aspect, there is provided a method of treating a condition of a lower leg of a subject, the method including:
 (A) locating a plurality of straps around a calf muscle of the subject;
 (B) locating a plurality of pressure nodes between the plurality of straps and the calf muscle, the plurality of pressure nodes configured to apply elevated pressure to a plurality of targeted zones of the calf muscle when one or more of the plurality of straps are tightened around the calf muscle;
 (C) wherein the plurality of targeted zones includes at least two of:
  (a) the approximate point on the calf where the soleus muscle attaches to the posterior head of the fibula;
  (b) the approximate point where the soleus muscle attaches to the middle third of the tibia; and
  (c) the back of the calf at approximately the junction of the Achilles tendon and the triceps surae muscle.

In one aspect, there is provided a calf brace for the treatment of a lower leg condition including:
 (A) a body component adapted to conform with a wearer's calf;
 (B) a torsional component which in use will apply a torsional force in an infero-medial direction to the wearer's calf;
 (C) an elongate compression member applying a pressure force to approximately a distal third of the medial border of the tibia; and
 (D) at least one pressure node which in use is located adjacent the wearer's calf so as to apply at a distinct point an elevated pressure at that point to the wearer's calf, said elevated pressure being maintained by the tightness of the body component around the wearer's calf.

In one aspect, there is provided a calf brace for the treatment of lower leg conditions of a wearer of the calf brace, the calf brace including:
 (A) a first strap adapted to be affixed around an upper portion of the wearer's calf;
 (B) a second strap adapted to be affixed around a generally central portion of the wearer's calf;
 (C) a torsional strap connecting the first and second straps which in use will apply a torsional force to the wearer's calf;
 (D) a third strap adapted to be affixed around a lower portion of the wearer's calf;

(E) a generally longitudinal strap connecting the second and third straps;
(F) an elongate compression member held by the longitudinal strap; and
(G) at least one pressure node which in use is located between a strap and the wearer's calf so as to apply at a distinct point an elevated pressure at that point to the wearer's calf, said elevated pressure being maintained by the tightness of the strap around the wearer's calf.

According to a preferred form of the invention there is provided a calf brace for the treatment of lower leg conditions comprising:

a first strap adapted to be affixed around the upper portion of a wearer's calf;

a second strap adapted to be affixed around a generally central portion of the wearer's calf;

a torsional strap adapted connecting the first and second straps which in use will apply a torsional force to the wearers calf;

a third strap adapted to be affixed around a lower portion of the wearer's calf;

a generally vertical strap connecting the second and third straps;

an elongate compression member held by the vertical strap; and at least one pressure node which in use is located between a strap and the wearer's calf so as to apply at a distinct point an elevated pressure at that point to the wearer's calf, said elevated pressure being maintained by the tightness of the said strap around the wearer's calf.

Preferably the brace includes three pressure nodes, one located between the first strap and the calf, one located between the torsional strap and the calf, and the third located between the second strap and the calf. The torsional strap preferably rotates the calf muscle in an infero-medial direction.

The elongate compression member may be in the form of a cylindrical rod, and in use will apply a pressure force to the medial border of the tibia.

The pressure node or nodes will preferably be formed in a hemispherical shape with the curved side facing the calf in use. The elongate compression rod is preferably of circular cylindrical shape and approximately 100 mm long applying pressure to the distal third of the tibia.

The position of the pressure nodes relative to the straps will preferably be adjustable.

These and further features of the invention will be made apparent from the description of a preferred embodiment of the invention given below with reference to the accompanying drawings. The specific features shown in the drawings should not however be construed as limiting on the invention.

DETAILED DESCRIPTION OF THE PREFERRED EMBODIMENTS

It is believed that MTSS in athletes, particularly runners, is caused by a combination of calf tightening causing increased pressure at musclo-tendinous junctions and calf torsion leads to periosteal elevation and subsequent inflammation and oedema causing pain and loss of function. It is further believed that applying pressure along the medial border of the tibia to compress the elevated periosteum and at the key musculo-tendinous junctions will help to reverse the pathophysiological process of MTSS and therefore treat and/or reduce the incidence of shin splints.

By releasing the calf muscle with a calf brace to be herein described, some relief of MTSS has been demonstrated by the present inventors. In addition to MTSS, there are a range of conditions of the lower leg, including the foot, that may benefit from releasing the calf muscle by wearing of a calf brace as will be herein described. These conditions include, without limitation, plantar fasciitis, delayed onset muscle soreness (DOMS), Achilles tendinopathy and even more generally, tightness and poor flexibility.

Figure 1:
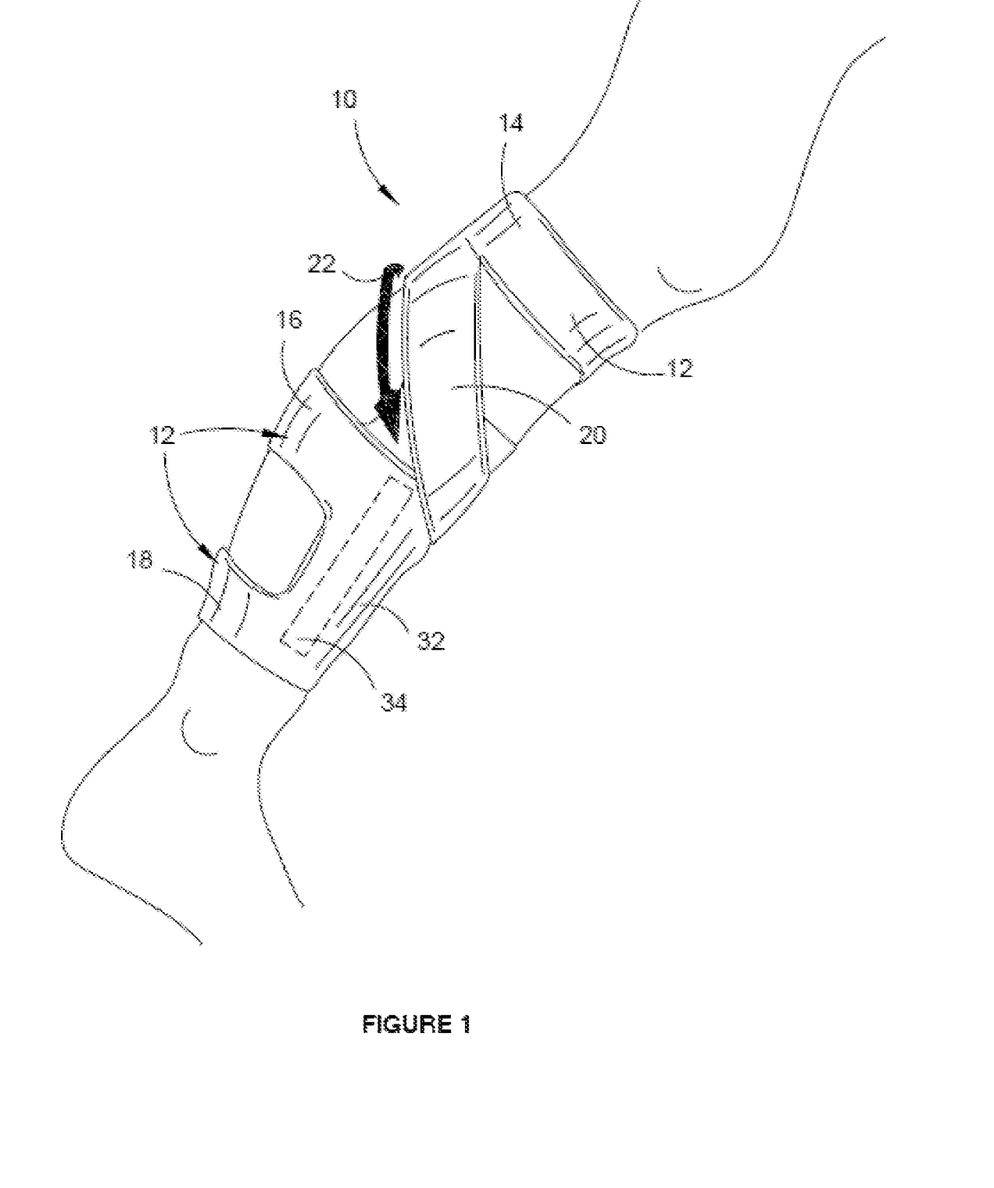
FIG. 1 shows a side medial view of a user's left calf with a brace according to the invention fitted thereto.
Figure 2:
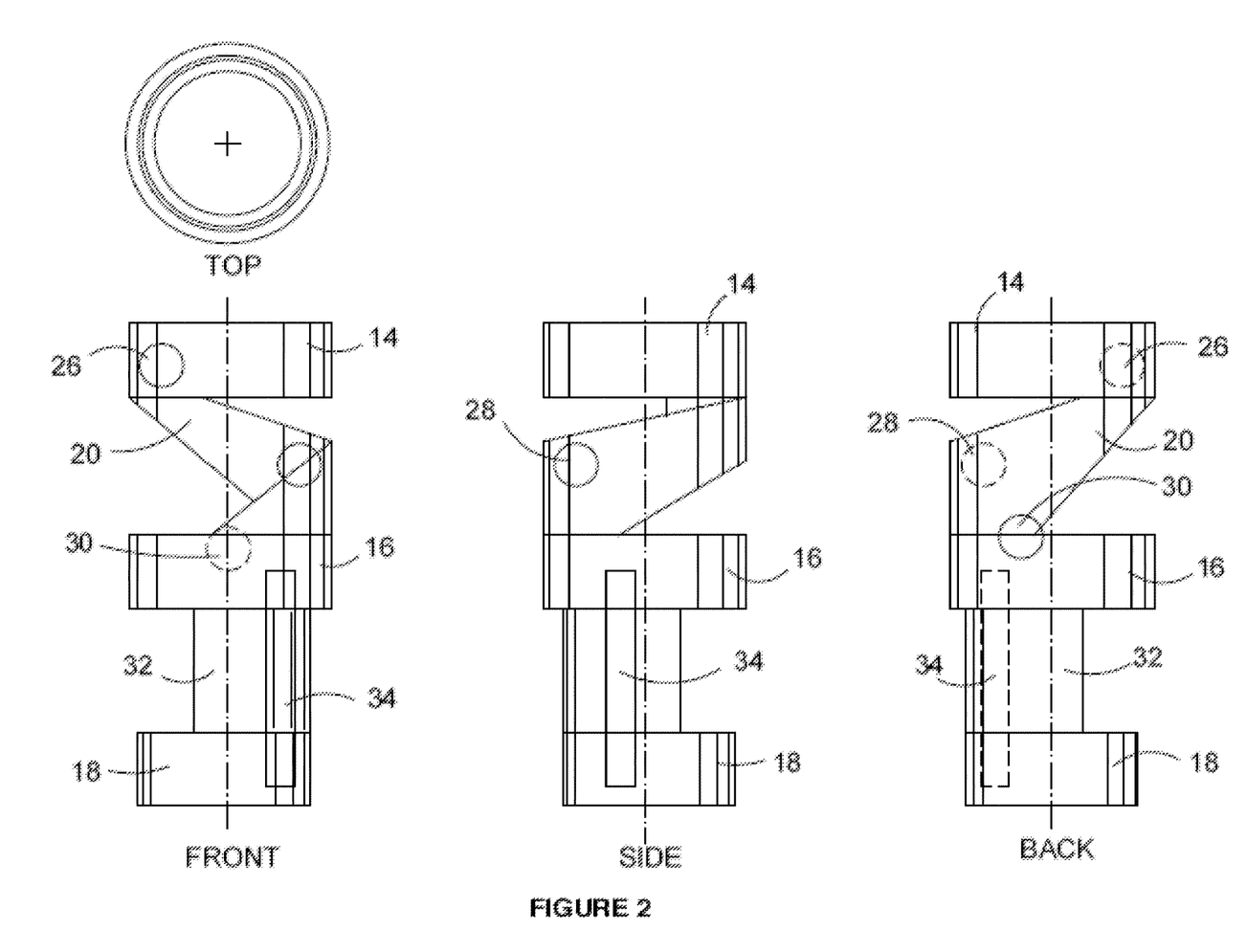
FIG. 2 shows a front, side, back and top views of the right calf brace.
Figure 3:
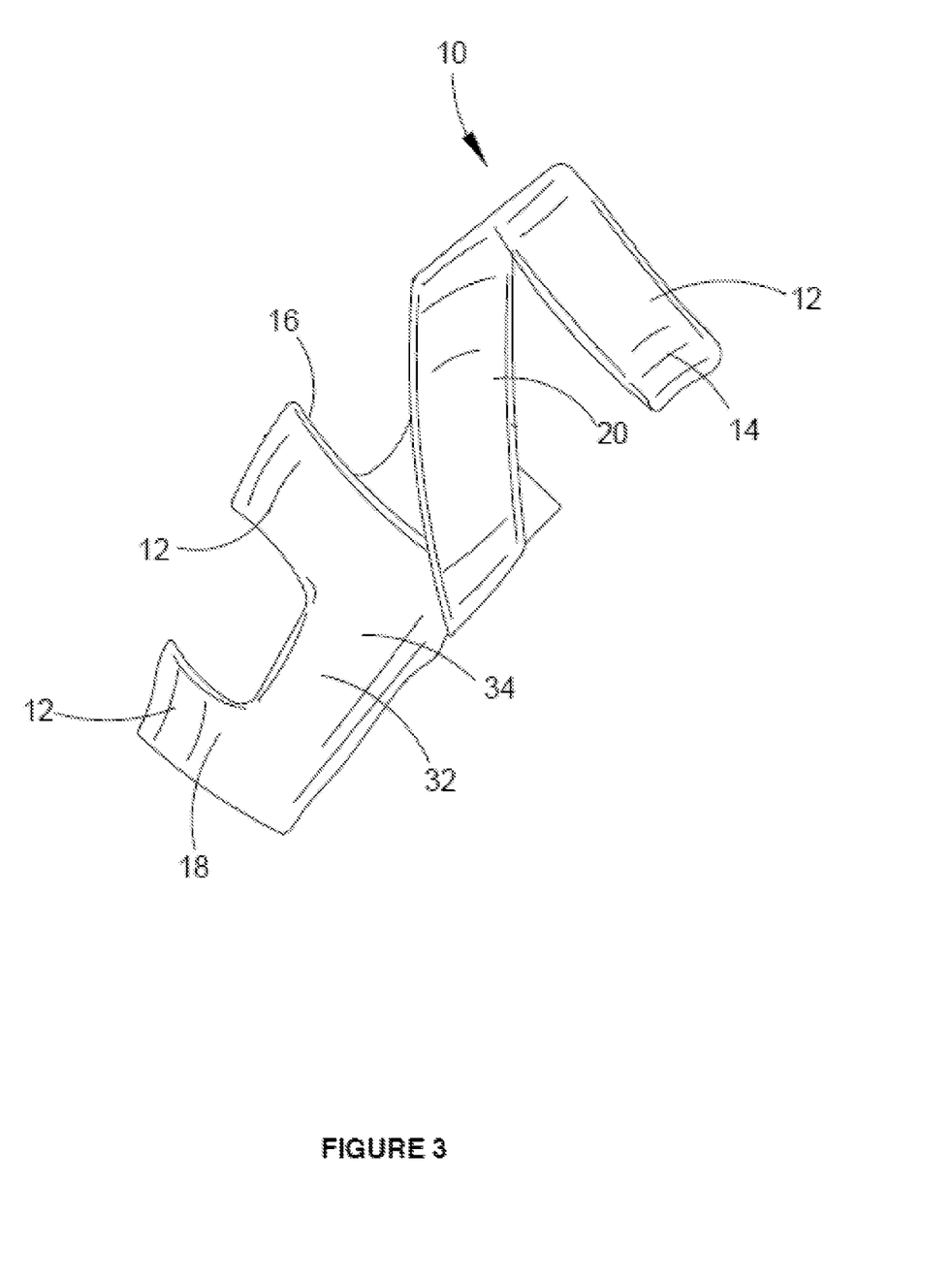
FIG. 3 shows a perspective view of a pressure node which forms part of the brace.

A calf brace 10 for the treatment of shin splints (MTSS) and other conditions of the lower leg is shown in FIGS. 1-3 of the drawings. FIGS. 1 and 3 depict a calf brace for a left leg. FIG. 2 depicts a calf brace for a right leg, being a mirror image of the left leg calf brace. The calf brace 10 may include three straps or bands 12 which circle the wearer's calf, as shown, an upper strap 14, a central strap 16, and a lower strap 18. The straps 12 are secured in position using a hook and loop fastening system (for example "VELCRO™"), allowing the taughtness of the straps to be adjusted. The straps 12 may be approximately 50 mm in width. The length of the brace, top to bottom, may be approximately 320 mm, for an adult male wearer though the calf brace 10 may be manufactured in a range of sizes to accommodate different leg lengths and calf diameters.

Connecting the upper strap 14 to the central strap 16 is a torsional strap 20 which is used to impart a torsional force to the calf muscle in the direction 22 as shown. To maintain the torsional force on the muscle the straps 12 will need to be sufficiently tightly applied, and have a non-slip inner surface to ensure they do not simply slip around and lose the torsional force applied by the torsion strap 20.

Three pressure nodes are positioned on the brace to apply increased pressure at specific points on the calf. An upper node 26 is located between the upper strap 14 and the calf at approximately the point on the calf where the soleus muscle attaches to the posterior head of the fibula. A second node 28 is located between the torsional strap 20 and the calf at approximately the point where the soleus muscle attaches to the middle third of the tibia. A third pressure node 30 is located between the central strap 16 at the back of the calf at approximately the junction of the Achilles tendon and the triceps surae muscle. The positions of one or more of the nodes may be adjustable to treat different patients.

In one embodiment, the nodes are of hemispherical shape, with the rounded side of the hemisphere facing inwards towards the calf. The hemispheres may be approximately 15 mm to 35 mm in diameter, and may be formed of a rubber or rubber-like material which will provide some compressibility, but will ensure that an elevated pressure is applied at the positions where the nodes are located. The hardness of the rubber will be selected to achieve a balance between applying effective pressure, yet not causing excessive wearer discomfort in use.

A vertical strap 32 connects the central strap 16 to the lower strap 18. The vertical strap 32 is arranged to support a rib or pressure rod 34 which in use will be aligned generally parallel to the length of the tibia and apply a compressive force to the medial border of the tibia. The compressive rod may be formed of a relatively hard rubber, plastic or metal. The rod 34 will be between about 75 mm to 150 mm, preferably around 100 mm, and have a diameter of between about 10 and 20 mm.

The various straps can be formed of any suitable flexible, non-stretch material that will not cause wearer irritation or discomfort. The outer layer of the straps may be made of neoprene (3 mm thick, 50 mm wide) that encases a latex band (1.5 mm thick, 50 mm wide). The brace is tightened using a simple wrap arrangement and secured using a hook and loop attachment arrangement that will, in the act of fitting the brace to the calf, produce the aforementioned torsional force. Once the brace has been fitted the three pressure nodes will be inserted between the straps and the calf at the aforementioned positions.

Whilst not wishing to be bound by theory, it is believed that a brace configured as above, with pressure nodes and the compression rod positioned where indicated will have the effect on the physiology of the calf as discussed below.

Dysfunction of the soleus muscle is commonly implicated in MTSS.

Additionally, muscle imbalance and inflexibility, especially tightness of the triceps surae (grastrocnemius, soleus, and plantaris muscles) has been documented heavily in the literature as being commonly associated with MTSS.

The reason the compression rod is provided as part of the brace is as follows. The pathophysiology is not well understood, however, it is believed to be a combination of tendinopathy, periostitis, periosteal remodelling, and stress reaction of the tibia with one of the key processes involved being periosteal elevation away from the bone caused by a pulling force applied by the calf muscles. Periosteum is a thin connective tissue that covers bone and is pain sensitive. For tendons to attach to bone, they must also attach to the periosteum.

The compression rod is designed to compress the distal one third of the medial border of the tibia where periosteal elevation and inflammation is thought to occur.

The reason an infero-medial torsion of the calf is applied by the torsional strap is as follows. As mentioned above, periosteal elevation and subsequent inflammation is thought to be partly due to calf tightening and pulling away of the periosteum. Due to the structure and points of attachment of the calf muscle, a tight calf pulls in a supero-lateral direction. By reversing the forces generated in calf tightening by applying an infero-medial torsional force it is envisaged that this will aid in reducing periosteal elevation and associated pain.

The calf brace may be worn immediately prior to and/or after exercise. The calf brace may also be worn during exercise, for example during warm up. In one treatment regime, it is considered that wearing the calf brace for ½ to 2 hours per day will provide therapeutic benefits. In one specific test, the knee-to-wall test was used to determine improvements in calf tightness. A subject undertook the knee-to-wall test prior to wearing the calf brace for 30-120 minutes and again after the calf brace was removed. In each case, the subject achieved improvements of 20-25% in the knee-to-wall test without additional physiotherapy or stretching.

It will be appreciated by the person skilled in the art from the simple knee-to-wall test example discussed above, that the calf brace may be used to treat a range of lower leg conditions, including, most simply, poor flexibility through the ankle and foot. Other conditions that may benefit include, without limitation, plantar fasciitis, delayed onset muscle soreness (DOMS), and Achilles tendinopathy.

It will further be appreciated by the skilled addressee that for some conditions and treatment regimes, it may not be necessary to combine all of the factors of three targeted pressure nodes, a compressive rod, and torsion, in order to achieve therapeutic benefits in the subject. A calf brace combining different subsets of these elements may help in alleviating different lower leg conditions. For example, the compressive rod is useful in treating MTSS by reducing periosteal tenting, compressing the periosteal fibres to improve healing pushing down the muscle fibres. However, this is not a factor in all conditions of the lower leg, such as plantar fasciitis or Achilles tendinopathy, and therefore in some embodiments, the compressive rod may be omitted. Likewise, the application of torsion may not be essential to treat all conditions. There are several conditions of the lower leg that show improvement by treatment to release the calf muscle and this can be achieved by a calf brace with pressure nodes that target different combinations of the three areas discussed above.

A further embodiment of the invention is depicted in FIGS. 4 to 10. In this embodiment, a sleeve or sock provides an easy support means for guiding the brace on to the wearer's calf. The sleeve provides an anchor point for a plurality of straps which in turn provide a means for securing and locating a pressure node at the appropriate relief points of the wearer's lower leg.

Figures 4A, 4B, 4C:
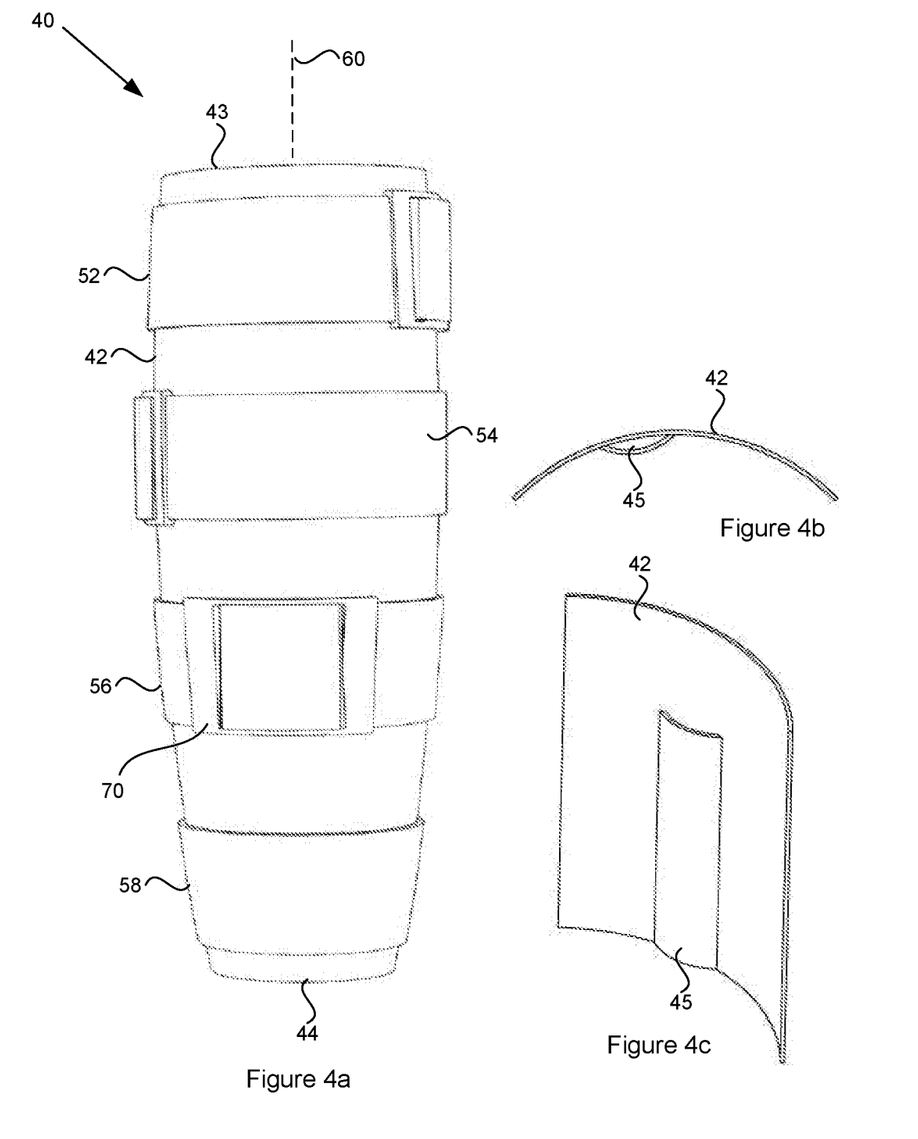
FIG. 4a shows a rear view of a right calf brace of an alternative embodiment.
FIG. 4b shows a top view of a section of the sleeve depicting a pocket for a compressive rod.
FIG. 4c shows an internal side view of the section of FIG. 4b.
Figure 5:
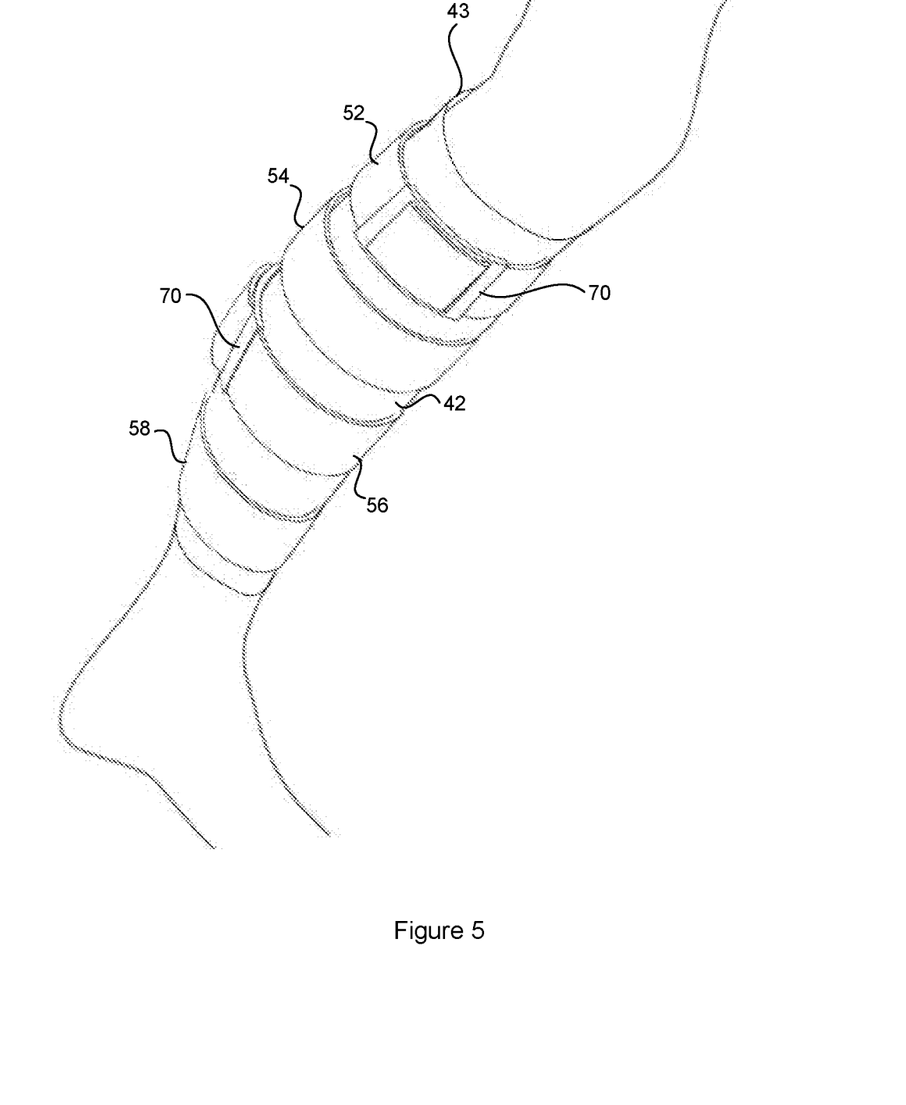
FIG. 5 shows the calf brace of FIG. 4 in use on a wearer's leg.

As shown in FIG. 4, the calf brace includes a sleeve 42. The sleeve is a tube of material such as cotton, neoprene, polyester, or various blends of fabric. The particular material can be chosen for its comfort, breathability, etc. when worn against the skin. The sleeve 42 includes a top opening 43 and a bottom opening 44. The sleeve 42 provides a body component. In use, the wearer inserts a foot through the top opening and the sleeve is pulled over the wearer's lower leg until the sleeve is located in the appropriate position on the wearer's calf (FIG. 5). The sleeve 42 substantially conforms to the wearer's calf muscle. As shown in FIG. 5, the sleeve is made to match the length of the wearer's calf region from above the ankle to below the knee such that the wearer's foot protrudes through the bottom opening 44 of the sleeve 42. It will be appreciated by the person skilled in the art that the bottom opening is not essential and instead, the sleeve may be made in the form of a sock without affecting the performance of the calf brace. The sleeve may also extend above the wearer's knee if required. The sleeve 42 has a substantially longitudinal axis as indicated by dashed line 60 in FIG. 4. In use, the longitudinal axis 60 aligns with the longitudinal axis of the wearer's leg, for example as defined by the tibia or fibula.

Sewn into the sleeve is a longitudinal pocket 45 that is able to receive the compressive rod.

The sleeve 42 provides a support and anchor point for a plurality of straps 52, 54, 56, 58. Each of the straps 52, 54, 56, 58 is secured to the support sleeve 42 by any suitable attachment including, without limitation, stitching, adhesives, studs, etc. The straps may be permanently or releasably attached to the support sleeve. In the embodiment depicted, the straps are stitched to the support sleeve along a seam that runs in a longitudinal direction with respect to the support sleeve. Multiple adjacent stitch lines may be provided for additional strength. The straps may be of any suitable width to receive and locate pressure node elements as will be described below. In one specific embodiment, the straps are 50 mm wide and may be made of a synthetic webbing material.

Figure 6:
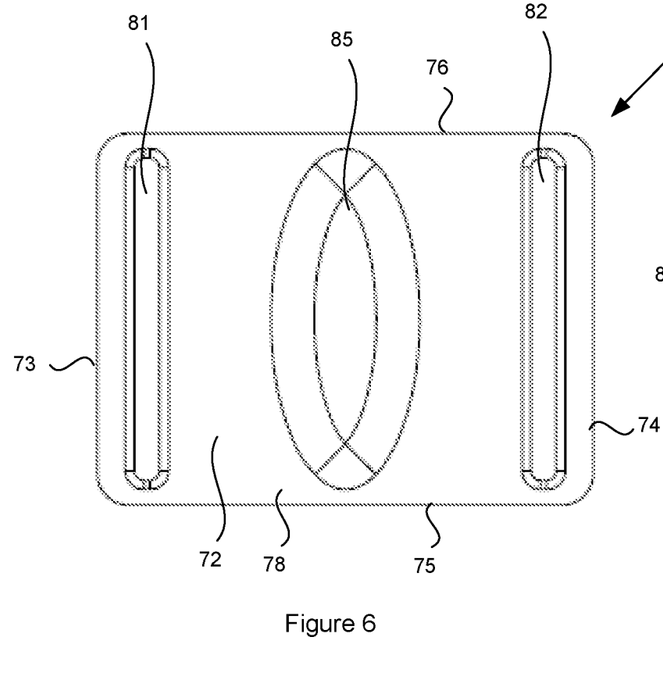
FIG. 6 shows a plan view of a pressure node element.
Figure 7:
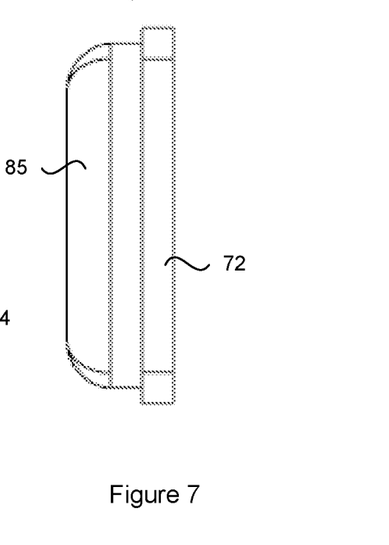
FIG. 7 shows an end view of the pressure node element.
Figure 8:
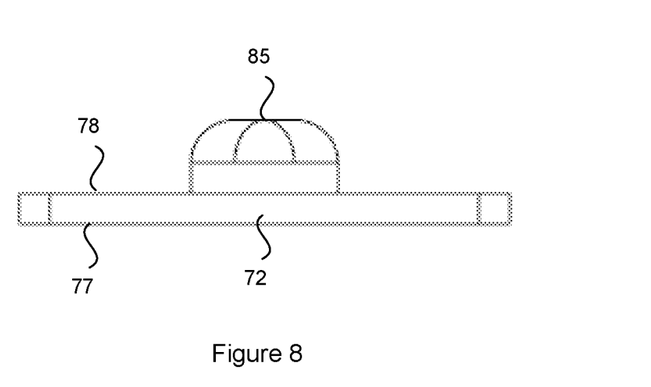
FIG. 8 shows an edge view of the pressure node element.

In use, the straps will conform to the wearer's leg and are used to locate pressure nodes at appropriate locations on the wearer's leg. The pressure nodes may be sown into the straps however this can limit the range of adjustability and make it difficult for the calf brace to accommodate various leg measurements of multiple wearers. In order to provide a more adjustable calf brace as well as allowing tailored fitting to a specific wearer, the pressure node may be provided on a removable element that can slide along the strap to the required position. A particular embodiment of a pressure node element is illustrated in FIGS. 6 to 8. The pressure node element 70 includes a base 72 that may be substantially rectangular. In one particular embodiment, the base 72 is approximately 80 mm×60 mm×5 mm thick, though the dimensions may vary. The base 72 includes ends 73, 74, edges 75, 76, and front and back faces 77, 78.

The base 72 includes a slot 81, 82 at each end that penetrates through the thickness of the base 72 and is long enough to receive a strap. In one embodiment, the straps are 50 mm wide and thus the slot may be approximately 53 mm long and 4 mm wide accordingly.

A pressure node 85 projects from the back face of the base. The base 72 and pressure node 85 may be integrally formed of the same material, e.g. rubber or rubber-like material. Alternatively, the pressure node 85 may be formed separately and secured to the base, e.g. by adhesives or other appropriate fastening mechanism. In the embodiment shown, the pressure node 85 has a hemi-ellipsoid shape. When viewed from either of the edges 75, 76, the pressure node appears substantially dome shaped (i.e. hemispherical). When viewed from the sides 73, 74, it can be seen that the dome is elongated across the width of the base 72. The hemi-ellipsoid pressure node in one embodiment has a length of approximately 55 m, which, in use, will extend in the longitudinal direction 60 of the calf brace. In this embodiment, the hemi-ellipsoid pressure node 85 has a width of approximately 24 mm which, in use, will align with the lateral direction of the calf brace. Wider pressure nodes, e.g. up to approximately 45 mm may also be used however the wider the pressure node, the less pinpoint the pressure exerted will be. The pressure node 85 projects approximately 12 mm from the back face 78 of the base 72.

The advantages of the hemi-ellipsoid will be discussed in more detail below. However, the person skilled in the art will readily understand that other shapes such as hemispherical, cylindrical, semi-cylindrical, square, rectangular, star shaped, etc. may be used and are contemplated within the scope of the invention in its broadest form. While example dimensions are given, other dimensions are possible with the emphasis being on the pressure node's ability to provide pressure to targeted areas of the wearer's calf.

Figure 9:
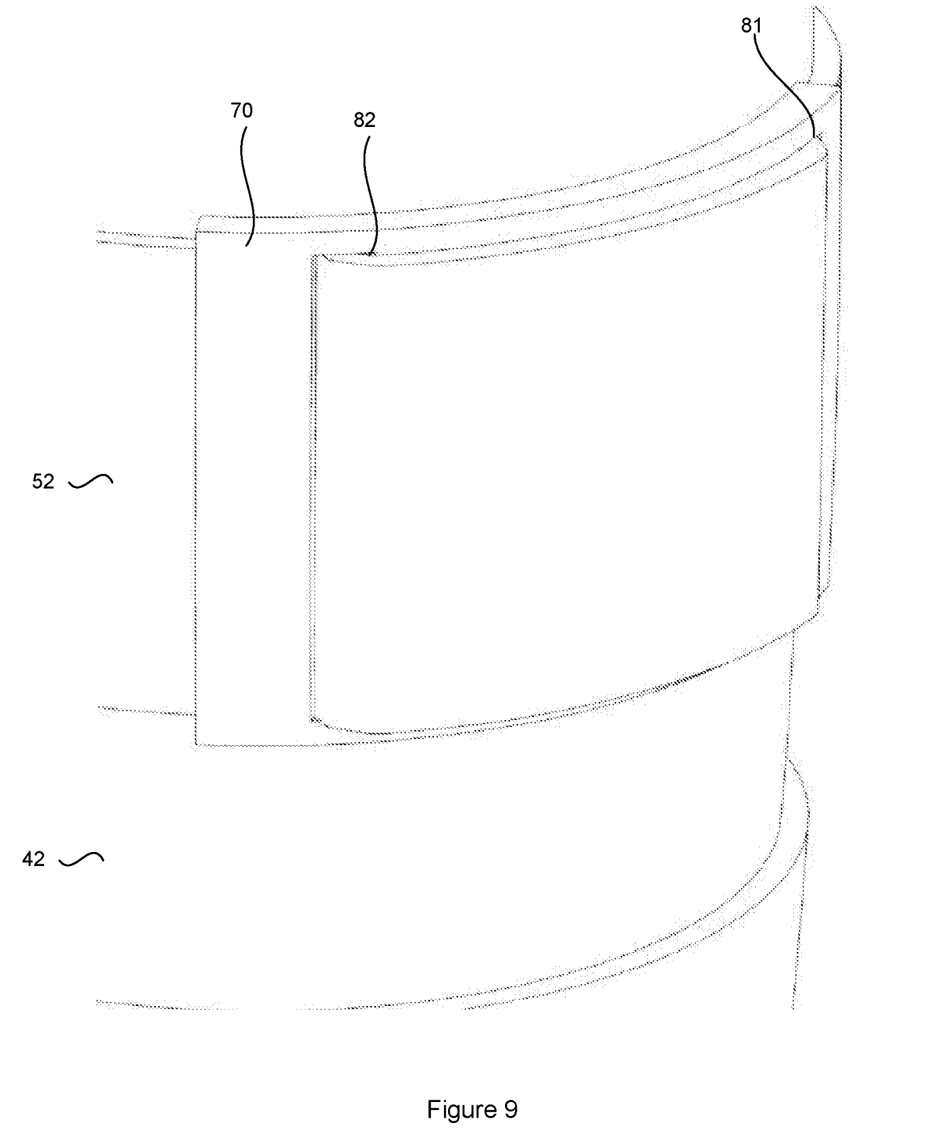
FIG. 9 shows the pressure node element engaging a strap.

FIG. 9 shows a close up view of one of the pressure node elements in location on the strap. The pressure node element 70 may be secured to the strap 52 (or equivalently straps 54, 56) with the pressure node 85 facing inward (see FIG. 10). An end of the strap 52 may be fed through a first one of the slots 81, 82 from the back or inner face 78. The strap then extends across the front face 77 and then through the other of the slots 81, 82. The straps may be provided with a securing mechanism such as hook and loop fastener, buckles, clips etc. that allows the strap to be tightened onto the sleeve around the wearer's calf.

Figure 10:
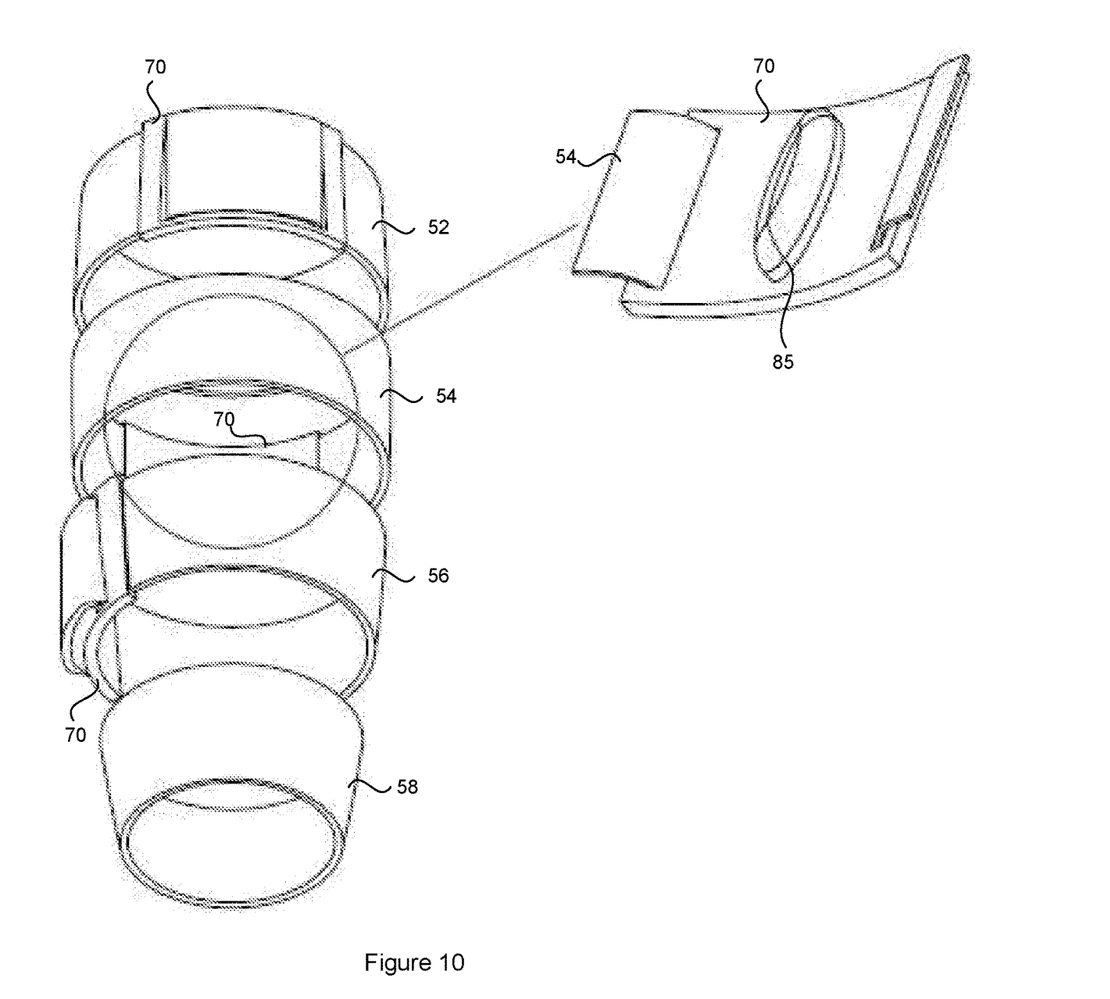
FIG. 10 shows a lower perspective view of the calf brace with sleeve omitted and depicting the strap configuration.

The calf brace of FIGS. 4 and 5 is depicted as having four straps secured to the support sleeve. FIG. 10 shows a lower perspective view of the straps with the sleeve 42 removed for clarity. The lower two straps 56, 58 are configured to hold or secure a compressive rod. In one embodiment, the straps 56, 58 may be fitted with narrow sleeves into which ends of the compressive rod may be inserted. Other attachment features such as elastic loops may also be used. Alternatively, the straps may more simply sandwich the compressive rod between the strap and the sleeve. Alternatively, the compressive rod may be sewn or otherwise provided directly into the sleeve 42, for example via a pocket sewn into the sleeve. The upper three straps 52, 54, 56 each receive a pressure node element 70 targeted to the pressure regions discussed above. As depicted in FIG. 10, the base 72 of the pressure node 70 is sufficiently pliable to substantially conform to the curve of the wearer's leg. While FIG. 10 shows the straps 52, 54, 56, 58 forming full circles, it is not essential for the straps to form full circles in order to locate the pressure nodes at the targeted areas. Shorter straps configured to extend partially around the wearer's calf and passing over the targeted areas may be sufficient.

The use of the calf brace 40 will now be described. A wearer inserts their foot into the top opening 43 of the sleeve and the sleeve 42 is pulled over the foot until the sleeve is covering the wearer's calf muscle (FIG. 5). The compressive rod may be used as an initial point of reference for aligning both the height and lateral position of the brace on the wearer's calf. The compressive rod may be substantially aligned with the distal third of the medial border of the tibia and then the lowest strap 58 may be tightened an initial amount to locate the calf brace 40 in position. Next, the pressure node elements 70 may be adjusted laterally along the length of their respective straps so that the pressure nodes 85 engage the desired treatment points of the wearer's calf. Finally, the straps may be tightened to provide the required amount of compression at the targeted pressure zones.

Figure 11:
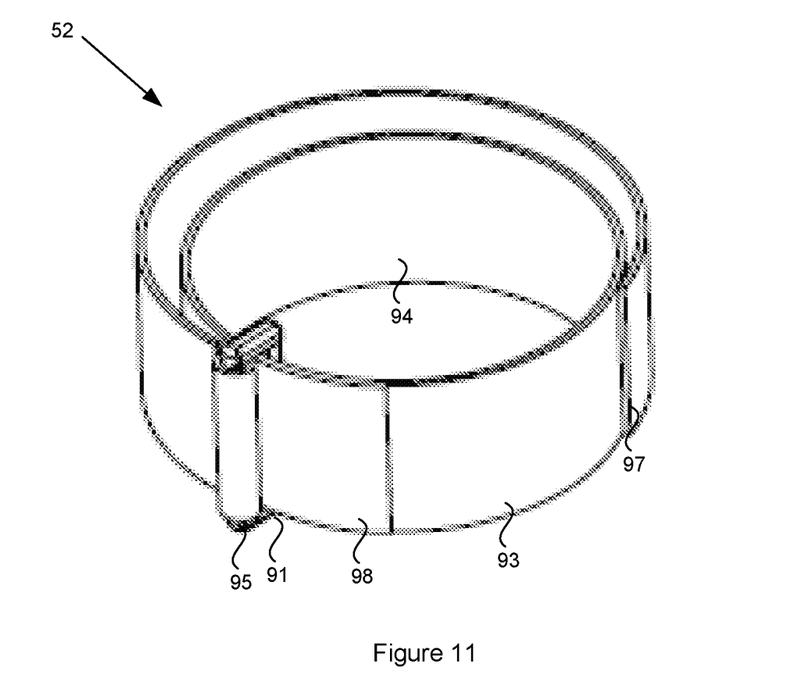
FIG. 11 shows a perspective view of a strap.
Figure 12:
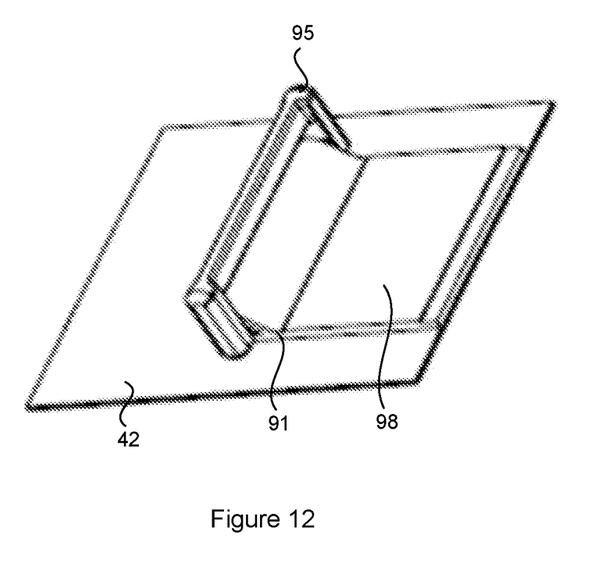
FIG. 12 shows a section of the strap attached to a sleeve.

The straps 52, 54, 56 are anchored to the sleeve such that as the strap is pulled and tightened, an additional torsion may be applied to the calf muscle to aid in the calf muscle release. For example, the straps may be anchored on the lateral side and then pulled around the back of the calf muscle toward the medial side to give torsion in the same direction as for the earlier described embodiments (arrow 22 in FIG. 1). In one specific embodiment (FIGS. 11 and 12), a strap, e.g. strap 52, is stitched into the sleeve 42 on the lateral side at a stitch point 91. The strap passes across the front of the leg 93 from the lateral to the medial side and around the back 94 (anticlockwise in FIG. 11). After a full circuit of the leg, the strap passes through a loop 95 at the stitch point 91. The loop 95 redirects the strap back around the back of the calf. As the strap is tightened through the loop 95, infero-medial torsion is applied to the calf. Hook and loop tabs at the end of the strap 97 and at the stitch point 98 may be used to secure the strap in the tightened position.

FIG. 5 shows the calf brace in use on a wearer's right leg from the outside (lateral view). In this view, the pressure nodes of the first 52 and third 56 straps are visible while the pressure node of the second strap 54 and the compressive rod are hidden. The pressure node of the top strap 52 may target the point on the calf where the soleus muscle attaches to the posterior head of the fibula. The pressure node of the second strap 54 may target the point where the soleus muscle attaches to the middle third of the tibia. The pressure node of the third strap 56 targets the back of the calf at approximately the junction of the Achilles tendon and the triceps surae muscle. Pinpointing of the target areas is preferred for optimal treatment, however precise location of the target areas can be difficult, particularly for the untrained user, and thus approximate location of the target areas, within 10 mm, 20 mm or 40 mm, may be sufficient. The accuracy required may also be dependent on various factors including the particular individual wearer, their condition, leg dimensions, etc.

It is the present inventors' belief that a high level of calf release occurs when all three of the trigger points are activated and may be further enhanced by medial torsion of the calf muscle created during tightening of the straps. The compressive rod reduces periosteal tenting, compressing the periosteal fibres to improve healing. The combination of these factors can assist in the relief of MTSS. A treatment regime for MTSS may therefore include periodically wearing the calf brace for a timeframe. In one regime, the calf brace may be worn for 30-120 minutes daily. Alternatively or in addition, the calf brace may be worn immediately before and after exercise.

As noted above, there are other conditions of the lower leg, including the foot, which may benefit from release of the calf muscle only. Thus, the compressive rod may be considered as optional for some treatment regimes as it only contributes to reduction of periosteal tenting, but is not believed to contribute substantially to calf release. Furthermore, while optimal calf release may occur when all three pressure nodes are utilized with additional torsion, in some embodiments and treatment regimes, fewer than three of the pressure nodes may be used, with or without torsion from the straps.

The calf brace herein described accommodates multiple configurations and treatment regimes by allowing the different pressure nodes to be added or removed as required. The lateral location of the pressure node can be adjusted by sliding the pressure node element along its respective strap until the pressure node aligns with the particular targeted pressure zone. Elongation of the pressure node longitudinally, i.e. in the direction perpendicular to the direction of lateral adjustment, increases the range of leg sizes that can be accommodated by a single sized calf brace while still targeting the pressure zones on the calf muscle. Having some length across the targeted zone increases the likelihood that pressure will be exerted on the targeted pressure zone by the pressure node.

The calf brace may be manufactured in a range of sizes to accommodate different leg lengths and calf diameters.

The invention is not limited to the exact configuration of brace as shown in the drawings, nor the shape and form of the pressure nodes are necessarily as discussed above. However, applying the forces in the areas described will, it is believed, significantly reduce the effects of MTSS and/or provide a treatment for various conditions of the lower leg. The brace is relatively easy to apply, and a user will, with some instructed practice, be able to fit the brace himself without difficulty. It will be appreciated that the exact configuration of the straps, how they connect together, and the location of the fastening system can be varied without departing from the scope of the invention.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein. It will further be understood that any reference herein to known prior art does not, unless the contrary indication appears, constitute an admission that such prior art is commonly known by those skilled in the art to which the invention relates.

What is claimed is:

1. A calf brace for treating a condition of a lower leg of a subject, the calf brace including:
    (A) a plurality of straps configured to extend around at least a portion of a calf muscle of the subject;
    (B) a plurality of pressure nodes that in use, are located between the plurality of straps and the calf muscle, the plurality of pressure nodes configured to apply elevated pressure inward to a plurality of targeted zones of the calf muscle when one or more of the plurality of straps are tightened around the calf muscle;
    (C) at least one pressure node element from which at least one pressure node projects, the at least one pressure node element including one or more slots for receiving one of the plurality of straps such that the position of the pressure node may be adjusted along the strap;
    (D) wherein the plurality of targeted zones includes at least two of:
        (a) the approximate point on the calf where the soleus muscle attaches to the posterior head of the fibula;
        (b) the approximate point where the soleus muscle attaches to the middle third of the tibia; and
        (c) the back of the calf at approximately the junction of the Achilles tendon and the triceps surae muscle.

2. The calf brace of claim 1 including a rod located inward of at least one of the straps, the rod extending in a substantially longitudinal direction with regard to the calf brace, the rod located so as to align, in use, with approximately the distal one third of the medial border of the tibia.

3. The calf brace of claim 1 including a torsion strap, wherein tightening of the torsion strap, in use, rotates the calf muscle in an infero-medial direction.

4. The calf brace of claim 1 including a sleeve that provides support for the plurality of straps.

5. The calf brace of claim 4 wherein at least one of the plurality of straps is attached to the sleeve such that tightening the respective strap, in use, applies torsion to the calf muscle.

6. The calf brace of claim 1 wherein at least one pressure node has a hemi-ellipsoid shape.

7. The calf brace of claim 6 wherein the hemi-ellipsoid shape is extended in a longitudinal direction.

8. The calf brace of claim 1 wherein the plurality of targeted zones includes three of:

(a) the approximate point on the calf where the soleus muscle attaches to the posterior head of the fibula;
(b) the approximate point where the soleus muscle attaches to the middle third of the tibia; and
(c) the back of the calf at approximately the junction of the Achilles tendon and the triceps surae muscle.

9. A method of treating a condition of a lower leg of a subject, the method including:
(A) locating a plurality of straps around a calf muscle of the subject;
(B) locating a plurality of pressure nodes between the plurality of straps and the calf muscle, the plurality of pressure nodes configured to apply elevated pressure to a plurality of targeted zones of the calf muscle when one or more of the plurality of straps are tightened around the calf muscle;
(C) wherein the plurality of targeted zones includes at least two of:
(a) the approximate point on the calf where the soleus muscle attaches to the posterior head of the fibula;
(b) the approximate point where the soleus muscle attaches to the middle third of the tibia; and
(c) the back of the calf at approximately the junction of the Achilles tendon and the triceps surae muscle.

10. The method of claim 9 further including:
(A) locating a rod between at least one of the straps and the calf muscle;
(B) aligning the rod with approximately the distal one third of the medial border of the tibia;
(C) tightening the respective at least one of the straps to cause the rod to apply pressure to approximately the distal one third of the medial border of the tibia.

11. The method of claim 9 including tightening the plurality of straps around the calf muscle of the subject in a manner that applies torsion to the calf muscle.

12. The method of claim 9 wherein the plurality of targeted zones includes three of:
(a) the approximate point on the calf where the soleus muscle attaches to the posterior head of the fibula;
(b) the approximate point where the soleus muscle attaches to the middle third of the tibia; and
(c) the back of the calf at approximately the junction of the Achilles tendon and the triceps surae muscle.

13. A calf brace for treatment of lower leg conditions of a wearer of the calf brace, the calf brace including:
(A) a first strap adapted to be affixed around an upper portion of the wearer's calf;
(B) a second strap adapted to be affixed around a generally central portion of the wearer's calf;
(C) a torsional strap connecting the first and second straps which in use will apply a torsional force to the wearer's calf;
(D) a third strap adapted to be affixed around a lower portion of the wearer's calf;
(E) a generally longitudinal strap connecting the second and third straps;
(F) an elongate compression member held by the longitudinal strap; and
(G) at least one pressure node which in use is located between a strap one of the straps and the wearer's calf so as to apply at a distinct point an elevated pressure at that point to the wearer's calf, said elevated pressure being maintained by the tightness of the strap around the wearer's calf.

14. The calf brace of claim 13 wherein the at least one pressure node includes three pressure nodes, wherein a first pressure node targets a point on the calf where the soleus muscle attaches to the posterior head of the fibula, wherein a second pressure node targets a point where the soleus muscle attaches to the middle third of the tibia, and wherein a third pressure node targets a junction of the Achilles tendon and the triceps surae muscle.

15. The calf brace of claim 13 wherein the torsional strap is configured to, in use, rotate the calf muscle in an inferomedial direction.

16. The calf brace of claim 13 wherein, in use, the elongate compression member applies a pressure force to the medial border of the tibia.

17. The calf brace of claim 13 wherein at least one of the pressure nodes is hemispherical.

18. The calf brace of claim 13 wherein at least one of the pressure nodes is a hemi-ellipsoid.

19. The calf brace of claim 13 wherein a position of the pressure nodes relative to the straps is adjustable.

20. The calf brace of claim 13 including a sleeve adapted to conform to the wearer's calf wherein the sleeve provides an anchor point for one or more of the first strap, second strap and third strap, and wherein the at least one pressure node includes three pressure nodes including a first pressure node located between the first strap and the calf, a second pressure node located between the second strap and the calf, and a third pressure node located between the third strap and the calf.

* * * * *